United States Patent [19]

McWhorter

[11] Patent Number: 4,986,289
[45] Date of Patent: Jan. 22, 1991

[54] PACKAGED PRE-CUT DENTAL FLOSS PRODUCT

[76] Inventor: Charles E. McWhorter, 17130 Saddlewood Rd., Monument, Colo. 80132

[21] Appl. No.: 927,046

[22] Filed: Nov. 4, 1986

[51] Int. Cl.$^5$ ............................................. A61C 15/00
[52] U.S. Cl. ..................................... 132/323; 206/63.5
[58] Field of Search ................... 132/89, 90, 91, 92 R, 132/92 A, 93; 206/63.5, 368, 369, 370, 620, 820

[56] References Cited

U.S. PATENT DOCUMENTS

| | | | |
|---|---|---|---|
| 2,522,794 | 9/1950 | Medof | 132/93 |
| 2,748,781 | 6/1956 | Collat | 132/93 |
| 2,896,639 | 7/1959 | Fleming | 132/93 |
| 3,800,812 | 4/1974 | Jaffe | 132/89 |
| 3,802,445 | 4/1974 | Wesley | 132/89 |
| 3,913,596 | 10/1975 | Stuart | 132/89 |
| 3,926,201 | 12/1975 | Katz | 132/91 |
| 4,335,731 | 6/1982 | Bora, Jr. | 132/89 |
| 4,403,625 | 9/1983 | Sanders et al. | 132/91 |
| 4,519,408 | 5/1985 | Charatan | 132/89 |
| 4,579,221 | 4/1986 | Corella | 206/63.5 |

Primary Examiner—Gene Mancene
Assistant Examiner—Adriene B. Lepiane
Attorney, Agent, or Firm—Timothy J. Martin

[57] ABSTRACT

A dental hygiene product in the form of a packet having a front panel and a back panel containing a pre-cut length of dental floss thread stored as a coil. The packet is severable into first and second packet portions, and opposite ends of the thread are affixed to respective packet portions which, after being severed, form grip tabs to facilitate withdrawal and use of the floss thread. A perimeter slit helps start the tearing of the packet. A plurality of packets may be constructed in strip-wise and matrix array configurations, and the packets may be separable along perforations. When constructed as a packet set, a single thread may define coiled portions for respective packets, and cuts may be made to sever the thread into thread units. A layer of tacky material may be disposed on a portion of the interior surface of one of the front and back panels to initially adhere the dental floss thread in a selected configuration on the interior surface of one of the panels.

16 Claims, 2 Drawing Sheets

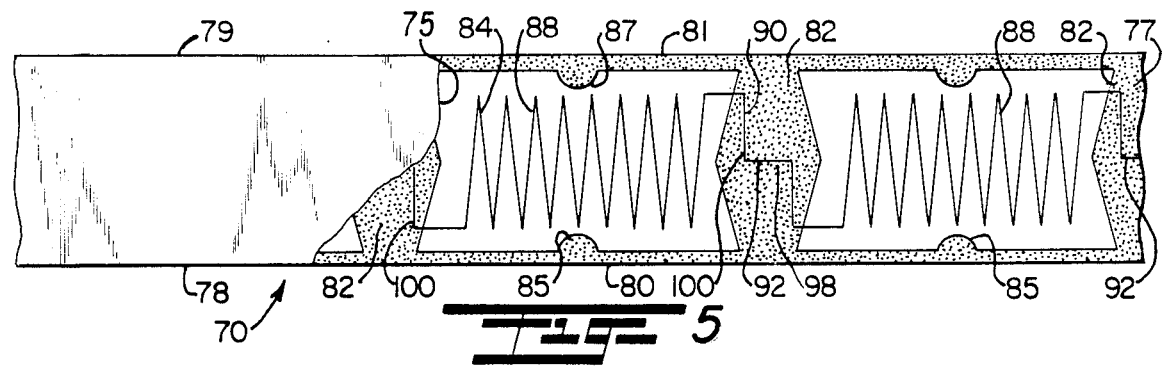
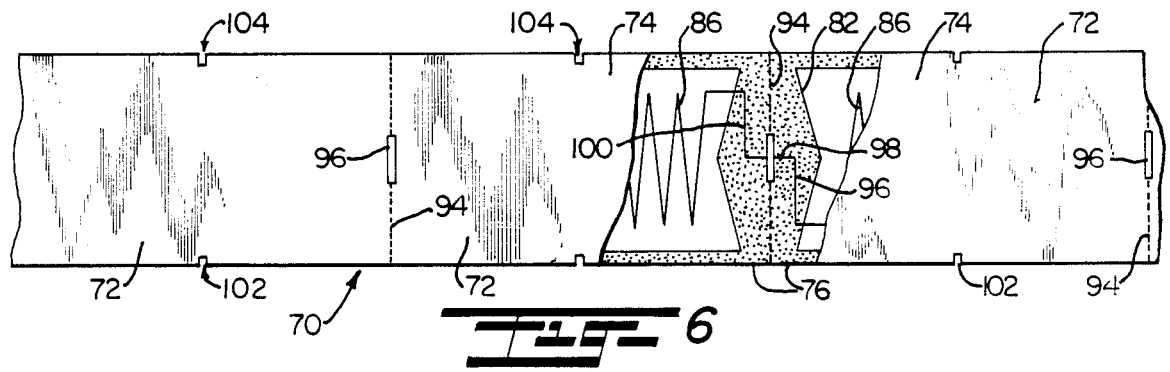
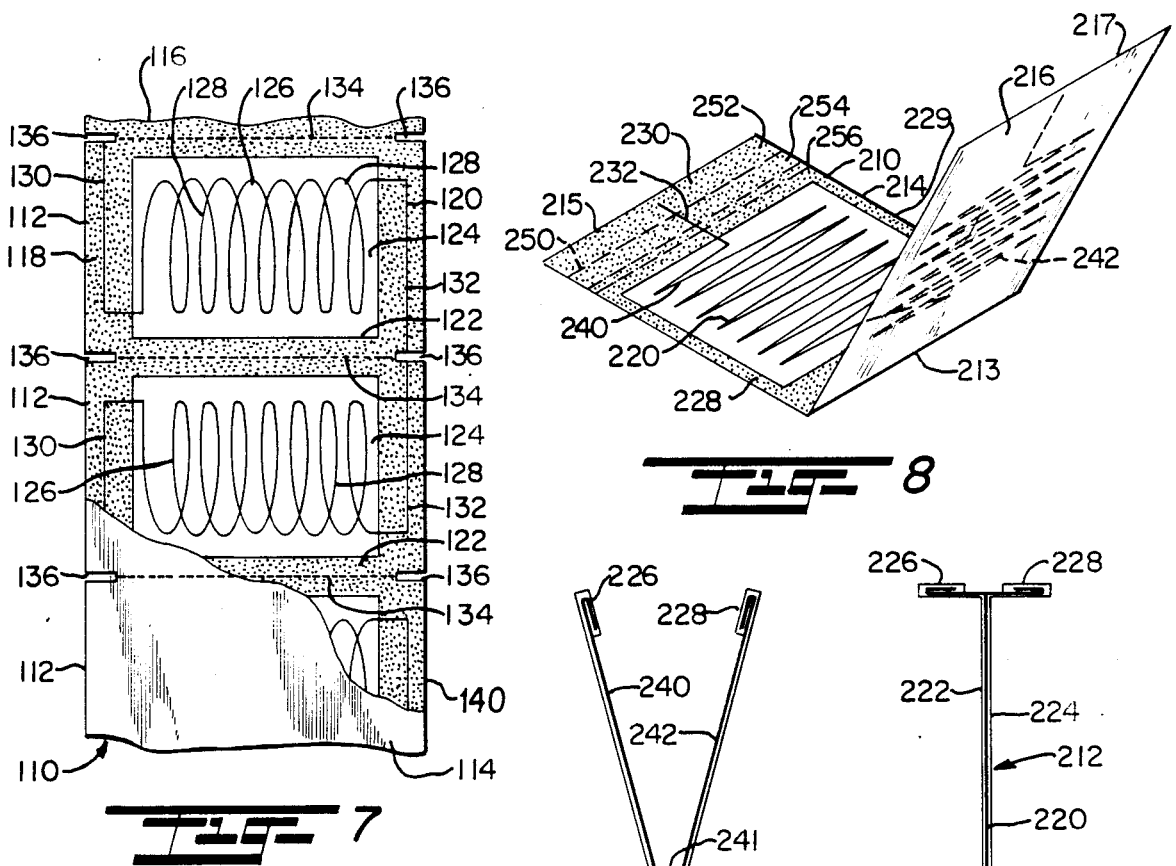

PACKAGED PRE-CUT DENTAL FLOSS PRODUCT

BACKGROUND OF THE INVENTION

The present invention generally relates to dental hygiene and is specifically directed to the provision of a dental floss product which is packaged as an individually dispensed unit of flossing thread. Accordingly, the present invention contemplates the provision of individualized packets containing a pre-selected length of dental floss rather than dental floss packaged as a bulk spool.

In the past, methods of cleaning one's teeth predominantly comprised the use of toothpicks or dental floss. Toothpicks are often packaged in bulk, but may be individually dispensed for a single use. Individualized dispensing includes either dispensing single toothpicks by means of a device which holds a quantity of loose toothpicks, or alternately through the dispensing of toothpicks that are contained in small, individually wrapped paper packages provided to ensure that the toothpick remains in a sanitary state.

Dental floss has commonly been manufactured and distributed as a spool of thread-like dental floss which is housed in a plastic dispensing container. The user withdraws a length of thread from the container and then severs the length from the spool. The user then wraps the thread about his or her fingers for manipulation and insertion of the thread between the teeth. Alternately, a length of flossing thread may be mounted on a flossing instrument, numerous ones of which have been developed in the past. An individual who seeks to employ flossing as a hygienic dental practice, commonly carries such a container housing a spool of flossing thread. Even though such containers may be relatively compact, they nonetheless often present undesirable bulk in a person's pockets.

While dental hygienists have increasingly come to recognize and advocate flossing as a superior procedure in the treatment of the teeth and gums, there has not, to the applicant's knowledge, been the development of a product which packages dental floss as a single unit or individualized thread of dental floss. Indeed, there has been an increasing need for a dental flossing product wherein individualized threads are pre-cut and packaged for unit use in such manner that the packages maintain the sanitary condition of the dental floss. There is additional need for packets which may either be readily carried in the pocket, billfold, or otherwise, or which packets may be dispensed at the point of sale for food items, much in the manner of packaged toothpicks. There is a further need for such a dental floss product constructed to facilitate use of the thread of dental floss during the flossing act.

SUMMARY OF THE INVENTION

It is an object of the present invention to provide a dental floss product wherein select lengths of flossing thread are pre-cut and packaged in a novel, useful and sanitary manner.

Another object of the present invention is to provide a dental floss product that eliminates the bulk of a conventional flossing container so that several pre-cut and packaged units may readily be carried in a small space or dispensed at the point of sale of food products.

It is yet another object of the present invention to provide a dental floss product which is inexpensive in manufacture and which may be conveniently distributed, especially at the point of sale of food products, so as to encourage the use of flossing as a hygienic dental procedure.

It is a still further object of the present invention to provide a dental floss product which may be packaged as consecutive packets on a spool with the packets connected to one another, yet which are separable from one another and which spool may be employed in available types of dispensing apparatus.

According to the the preferred form of the present invention, then, a dental hygiene product is provided that includes a packet that is formed by a front panel and back panel secured together to define an enclosure that has an interior. The panels are constructed of a severable material so that the packet may be torn into first and second packet portions. Each packet stores a thread of dental floss of a pre-cut selected length in its interior. The thread of floss has a first end secured to the first packet portion and has a second end secured to the second packet portion; thus, when the packet is severed, the thread may be withdrawn from the ruptured enclosure so that the first and second packet portions form holding tabs to facilitate the manual gripping of the first and second ends of the dental floss thread during use.

With greater detail, the preferred embodiment of the present invention provides approximately ten to eighteen inches of dental floss which is positioned within the tearable packet in a zig-zag configuration, although both coiled and helical storing configurations are also contemplated. To facilitate the coiling of the thread of dental floss, an interior surface of the enclosure may include a material to which the thread of floss adheres, and the floss may be impregnated with a variety of materials, such as flavorings, flouride and the like. The packet may be provided with a slit along its peripheral edge to facilitate the initial tearing and as a guide to separate the packet into fairly equally sized packet portions. The front and back panels may be formed by common geometrical shape with the panels being adhered to one another around their common perimeter by means of glue or other adhesive, and this glue may simultaneously secure the opposite ends of the floss thread to the packet portions.

Preferably, a plurality of packets are formed by means of two ribbons of paper which are glued together and perforated to define a strip of packets secured together in edge-to-edge relationship yet which packets are separable from one another along the perforations. As the strip of packets is constructed, a continuous thread of dental floss may extend from packet to packet so that a unit thread portion is located within each packet when the ribbons of paper are secured together. When the packets are perforated, a cut is made between the packets which corresponds to the location of the thread that extends between adjacent packets; the thread is severed thereby leaving the unit thread portion within each packet.

These and other objects of the present invention will become more readily appreciated and understood from a consideration of the following detailed description of the preferred embodiment when taken together with the accompanying drawings, in which:

BRIEF DESCRIPTION OF THE DRAWINGS

FIG. 5 is a top plan view, partially broken away, showing a strip of packets according to the preferred embodiment of the present invention prior to being perforated;

FIG. 6 is a top plan view of the packets shown in FIG. 5, partially broken away, showing the packets after perforation;

FIG. 7 is a top plan view, partially broken away, of an alternate arrangement of the strip of packets according to the present invention, and showing a helical storing of the flossing thread therein;

FIG. 8 is a perspective view of an alternate embodiment of the dental floss packet according to the present invention shown in a pre-assembled state;

FIG. 9 is an edge view in elevation of the packet shown in FIG. 8, partially assembled;

FIG. 10 is an edge view in elevation of the packet shown in FIGS. 8 and 9 after assembly.

DETAILED DESCRIPTION OF THE PREFERRED EMBODIMENT

The present invention relates to a new and useful dental hygiene product in the form of pre-packaged dental floss wherein a pre-cut, selected length of dental floss is stored in a severable packet. This packet is small in size, and, since it is quite thin, the packet may be readily carried in wallets, billfolds, and the like. Since it is inexpensive, it is contemplated that this packet may be used as a replacement for complimentary toothpicks at the point of sale purchase of food products, for example, in restaurants, and may therefore stimulate the practice of flossing which has been demonstrated to be a preferred dental hygiene procedure. Indeed, the present invention may be inexpensively manufactured as a strip of a plurality of packets, connected in end-to-end relation, so that each packet may be consecutively removed from the strip for individual use.

Figure 1:
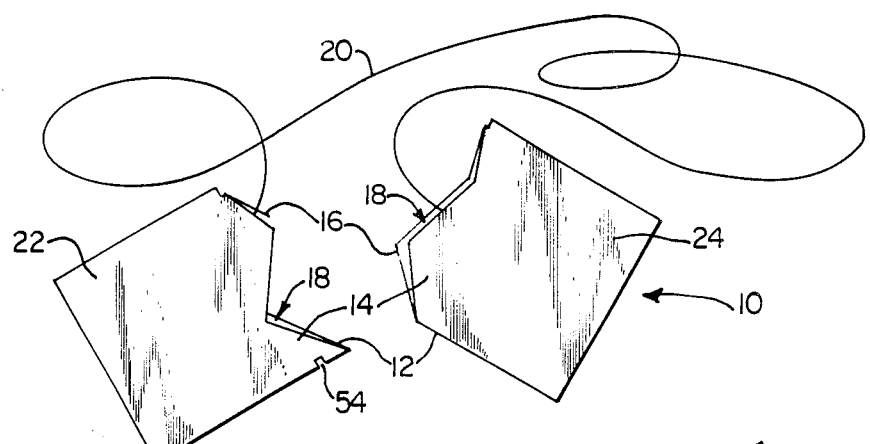
FIG. 1 is a perspective view of the packaged dental floss product according to the preferred embodiment of the present invention with the product being shown as separated into two packet portions.

As is shown in FIG. 1, the dental hygiene product 10 according to the preferred embodiment of the present invention broadly comprises a packet 12 formed of a front panel 14 and a back panel 16 which are secured together around a common perimeter to define an enclosure that has an interior 18. A strand or thread 20 of dental flossing material is mounted in packet 12, and FIG. 1 shows thread 20 being withdrawn from packet 12 as a precourse to utilization. To this end, packet 12, as is shown, in FIG. 1, is severable into first and second packet portions 22 and 24. These portions 22 and 24 define tabs which may be gripped by the fingers of the user so that thread 20 may readily be manipulated for performing the flossing act. Packet portions 22 and 24 thus obviate the inconvenient practice of initially wrapping the ends of the dental floss thread about the fingers of the user which is both an inconvenient and sometimes painful technique used by persons who seek to utilize the relatively fine and slippery dental floss thread which has no such tab grips.

Figure 2:
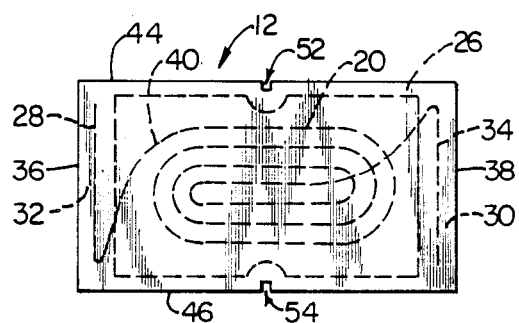
FIG. 2 is a top plan view of the packet shown in FIG. 1, prior to its being torn into the two packet portions.
Figure 3:
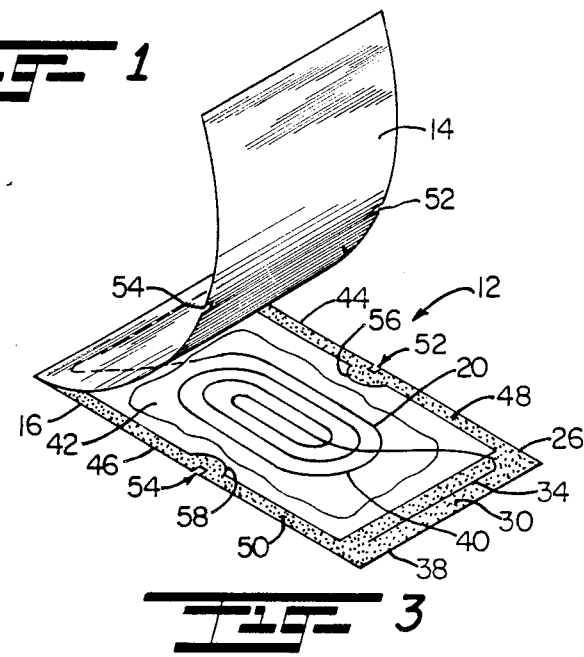
FIG. 3 is a perspective view of the packet shown in FIG. 2 with the front and back panels partially separated.

The construction of packet 12 according to the preferred embodiment of the present invention is more clearly shown in FIGS. 2 and 3. In these figures, it can be seen that packet 12 is constructed by two rectangular sheets or panels of material, which are preferably a tearable material such as paper. These panels 14 and 16 are secured together by means of an adhesive material, such as adhesive band 26 formed on one of the facing surfaces of panels 14 and 16 adjacent their common perimeter. It is entirely within the scope of this invention to use other types of edge seals, such as mechanical seals, heat seals and the like.

Band 26 includes margins 28 and 30 of adhesive formed on the opposite edges of packet 12 with margins 28 and 30 being of sufficient width to readily receive and adhere ends 32 and 34 of thread 20 when panels 14 and 16 are adhered together. To this end, thread 20 is mounted in packet 12 by placing an end portion 32 along edge 36 of packet 12, within the body of adhesive margin 28 after which thread 20 is turned back at an acute angle so that it is coiled into coiled mass 40 at a central location within packet 12. Coiled mass 40 then terminates in end portion 34 as an extension from the central portion of packet 12 to a corner thereof. End portion 34 is turned at an acute angle so that it lays generally parallel to edge 38 of packet 12, with end portion 34 of thread 20 lying within the body of adhesive margin 30.

In order to facilitate the initial placement of coiled mass 40 on the interior of packet 12 prior to the sealing of the common perimeter of panels 14 and 16 together by adhesive band 26, a tacky adhesive layer 42 may be applied to the central portion of a selected one of the panels so that it will initially retain coiled mass 40 thereon during packaging. Layer 42 may be an evaporative type of adhesive so that, after assembly of packet 12, this adhesive may either dissipate or be absorbed into the paper so that thread 20 is freely available to be withdrawn when packet 12 is severed into packet portions 22 and 24. Instead of dissipating, layer 42 could, if desired, be of sufficient tackiness to always retain coil 40, during normal storage, yet which does not substantially resist the forceable withdrawal of thread 20 during use. An alternate method for packaging could include the step of placing the adhesive directly on thread 20 rather than forming layer 42; however, the adhesive must be selected to avoid degrading the floss thread.

When assembled, packet 12 defines an enclosure which is formed by the securing of front panel 14 and rear panel 16 along a common perimeter formed by edges 36 and 38, as well as sides 44 and 46. To this end, the adhesive band 26 includes margins 48 and 50 at edges 44 and 46, respectively. It should be appreciated, however, that in construction it may be desirable that front and back panels 14 and 16 be constructed of a single piece of material which is folded about one edge so that one of adhesive margins 28, 30, 48 and 50 may be eliminated, it being sufficient that adhesive be placed within the interior of packet 12 sufficient to hold the end portions 32 and 34 of thread 20. Further, as noted above, it is desired that the user tear packet 12 into two packet portions 22 and 24, both to withdraw thread 20 from packet 12 and so that portions 22 and 24 provide gripping tabs. To facilitate this tearing, packet 12 is provided with a first slot 52 cut into edge 44 and a second slot 54 cut into edge 46. These slots provide an initial means for both starting the severing of packet portions 22 and 24 as well as to guide the tearing of the material so that first and second packet portions 22 and 24 are fairly similar in size. In order that the interior 18 of packet 12 be maintained in a clean, sealed manner, respective adhesive bands 44 and 46 include band portions 56 and 58, respectively, about slots 52 and 54.

From the above description, it should be appreciated that the user of the dental hygiene product 10 according to the present invention simply grasps opposite end portions of packet 12 and tears the packet 12 into the first and second packet portions 22 and 24 by a tearing motion through one of slots 52 and 54. This tearing can be completed even though end portion 32 of thread 20 is firmly secured by glue margin 28 in first packet portion 22 while the opposite end portion 34 of thread 20 is firmly affixed by glue margin 30 in second packet portion 24. Thread 20 may then be withdrawn from packet portions 22 and 24, by moving them apart, with packet portions 22 and 24 forming grip tabs for facilitating manual gripping of the end portions of thread 20. Packet portions 22 and 24 may be moved apart so that thread 20 becomes taut and the user may commence the flossing act in the standard manner. This invention accordingly provides a pre-cut length of dental floss that is preferably 10" (25.4 cm) to 18" (45.7 cm) in length, and it may have any selected thread diameter acceptable to the dental profession. This flossing thread, if desired, may be impregnated with flavoring, such as fruit, mint, spices and the like, which flavoring may be carried by a vegetable oil base. Also, the thread can be impregnated with a desired dental flouride compound.

Figure 4:
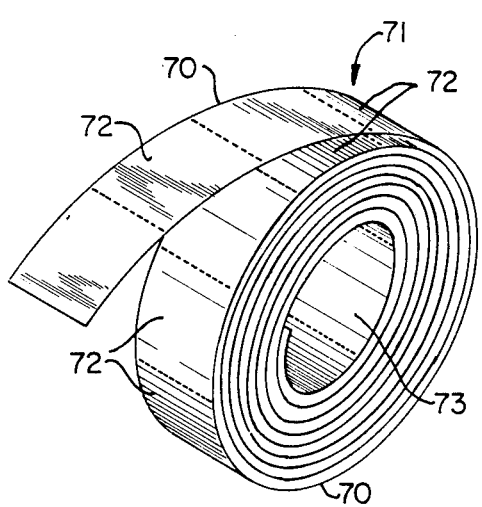
FIG. 4 is a perspective view of a spool of dental floss packets.

Another embodiment of the present invention is shown in FIGS. 4 through 6 wherein it is contemplated that, during manufacture, a plurality of packets 72 are formed as a continuous strip 70 of packets which may be wrapped into roll 71, shown in FIG. 4, for convenient dispensing, for example, at a point of food purchase. To this end, roll 71 may have an opening 73 which is provided so that roll 70 may be mounted on a rotating axle of pair of trunion pins provided by any convenient dispensing apparatus, such as those known in the art for rolls of tape and the like.

As is shown in FIGS. 5 and 6, packet strip 70 is preferably formed by front and back ribbons 75 and 77 which form front and back panels 74 and 76, respectively, for each successive packet 72. Front ribbon 75 and back ribbon 77 are secured together along edges 78 and 79 by means of glue margins 80 and 81, respectively. At spaced intervals along strip 70, front and back ribbons 75 and 77 are also adhered by transverse glue masses 82 which extend between margins 80 and 81. Glue masses 82 are diamond-shaped, and have a wider mid-portion located along the longitudinal axis of strip 70.

Each of packets 72 has an interior similar to that described with respect to packet 12, and each packet contains a discreet unit of flossing thread. In manufacture, it is preferable that each of the discreet, individual units 86 of flossing thread be formed of a single thread 84 of floss which is subsequently severed, as described below. As is shown in FIG. 5, thread 84 is mounted between ribbons 75 and 77 and includes consecutive zig-zap coils 88 between consecutive glue portions 82 with each of coiled masses 88 being interconnected by a central stair-step thread portion 90 which includes a wide, longitudinal portion 92 located centrally of each glue mass 82. Coils 88 are provided as that portion of the flossing thread which will be used as an individual unit in the act of flossing, and central portions 90 will form respective end portions for each of the units of thread 86 contained in each packet 72 after the completion of manufacture.

After thread 84 is placed between ribbons 75 and 77 as described above, ribbons 75 and 77 are adhered to one another as a precourse to forming individualized packets 72 which contain thread units 86. After completing this initial phase of construction, shown in FIG. 5, ribbon 70 is passed through a cutting machine which places perforations 94 transversely across strip 70 at a location which corresponds to the location of each glue mass 82. Perforations 94 include a wide slit 96 which operates not only to provide a perforation through strip 70, but also cuts each central longitudinal portion 92 of thread 84 so that, when the perforations 94 are formed, slit 96 severs thread 84 at each longitudinal portion 92 to form individual units 86 of flossing thread. Further, with reference to FIG. 6, it can be seen that each of glue masses 82 define glue margins at each end of successive packets 72 with the glue margins being formed from adhesive glue mass 82 being similar to margins 48 and 50, described above. These glue margins then secure opposite and facing end portions 98 and 100 of each thread unit 86.

From the foregoing, it should be appreciated that, upon construction, strip 70 thus is configured as a plurality of packets 72 which are individually defined by successive transverse perforations 94, and that each packet 72 may be removed from the strip by tearing the packet from the strip at each perforation 94. Accordingly, each packet 72 then is formed by front and back panels 74 and 76 which were formerly portions of the continuous ribbons 75 and 77, with each of the front and back panels 74 and 76 being secured to one another about a common perimeter. Each individual unit of thread 86 is contained within each packet 72 with each thread unit 86 having opposite ends secured to opposite ends of the respective packet 72 by means of a margin portion of glue that was formerly part of diamond-shaped glue mass 82. A plurality of slots 102 and 104 are formed in edges 78 and 79 of strip 70, and are similar to slots 52 and 54, described above. Accordingly, each adhesive margin 80 and 81 include enlarged portions 85 and 87 at the location of each slot 102,104. Each packet 72, in use, may be torn about slots 102,104 in a manner identical to that with respect to slots 52,54 above. Thus, each packet 72 is separated into two packet portions similar to packet portions 22 and 24, described above. Further, a strip of packets may be removed from the spool and carried as an accordion array, if desired.

FIG. 7 shows an alternate construction for a continuous strip of packets. In FIG. 7, a plurality of packets 110 are secured together along a common side, rather than in the end-to-end relation shown in FIGS. 4 through 6. The construction and manufacture of strip 112 of packets 110 is virtually identical to that described with respect to FIGS. 4–6, with the exceptions noted below. Specifically, as is shown in FIG. 7, strip 110 is formed by front and back ribbons 114 and 116 which are secured together by means of wide glue margins 118 and 120. Glue margins 118 and 120 are, at spaced locations, interconnected by transverse glue bands 122 so that a central area 124 is formed. A plurality of thread units 126 are formed out of a single thread, as described below, with thread units 126 including helically coiled portions 128 and first and second end portions 130 and 132. End portions 130 and 132 are secured in respective glue margins 118 and 120.

Each of packets 112 is defined by transverse perforations 134 which includes edge cuts 136. During manufacture, and prior to forming perforations 134 and edge cuts 136, each of thread units 126 is formed by a continuous thread of dental floss with a portion of the thread extending along respective edges 138 and 140 of strip 110. When cuts 136 are formed during the perforating operation, cuts 136 sever this continuous thread into the discreet thread units 126 in a manner similar to that described with respect to FIGS. 4–6. Thus, it should be appreciated, that again the ends of the thread units for adjacent packets 112 are in facing relationship to one another, across their respective slit 136. Use of each packet 112 is similar to that described with respect to packets 12 and 72, however, it should be noted, that no initial tearing slot such as slots 54 and slots 102 are provided.

FIGS. 8–10 show another embodiment of the present invention. In this embodiment, a packet 212 is shown in FIG. 10 as a finally constructed dental hygiene product. Packet 212 includes first and second packet portions 222 and 224 which have folded ends 226 and 228, respectively, which may be gripped by the user. Upon pulling folded end portions 226 and 228 apart, packet 212 is separated into packet portions 222 and 224 which releases dental flossing thread 220.

As is shown in FIGS. 8 and 9, in order to form packet 212, a single sheet of tearable material 210, which is in a rectangular configuration, is folded about line 213 to form front and back panels 214 and 216, respectively. Sheet 210 thus has edges 215 and 217 for each panel portion 214 and 216 with edges 215 and 217 being opposite fold 213. A glue band 228 extends around the common perimeter of panels 214 and 216 when they are folded together with glue margin 229 including a wide transverse margin portion adjacent each edge 215 and 217 of panel portions 214 and 216 respectively. For example, transverse glue margin 230 is shown adjacent edge 214. A first end portion 232 of thread 220 extends longitudinally of panel 214 and then forms a first zig-zag mass or coiled mass 240. A similar zig-zag coiled mass 242 of thread 220 is formed on the interior surface of panel 216, facing panel 214. Coiled masses 240 and 242 are interconnected by strand 241 of thread 220, shown in FIG. 9. It should be appreciated that coiled mass 242 is constructed similarly to mass 240 and includes an end portion that extends along a similar glue margin adjacent band 217. The respective edges 215 and 217 of panels 214 and 216 are then counter folded into end portions 226 and 228, as is shown in FIGS. 9 and 10. This counter folding is the same for both of edges 215 and 216 so that it will be accordingly described with respect to edge 215. As is shown in FIG. 8, edge 215 is first folded along fold line 250 so that end portion 230 is trapped between panel portions 252 and 254. The resulting adhered panel portions 252 and 254 are then reverse-curve folded about fold line 256 so that end portion 232 will form a double reverse curve about itself.

After each of ends 215 and 217 are folded, in the manner described, panel portions 214 and 216 are adhered together so that each of coiled masses 240 and 242 are sealed within the interior of packet 212 by perimeter glue margin 228. As is shown in FIG. 10, the edge portion 260 adjacent fold edge 213 is then severed from the adhered panel portions so that packet 212 is formed. The user then simply pulls apart portions 226 and 228 to separate packet portions 222 and 224, which correspond to front and back panels 214 and 216 thereby withdrawing thread 220 from packet 212.

Figure 11:
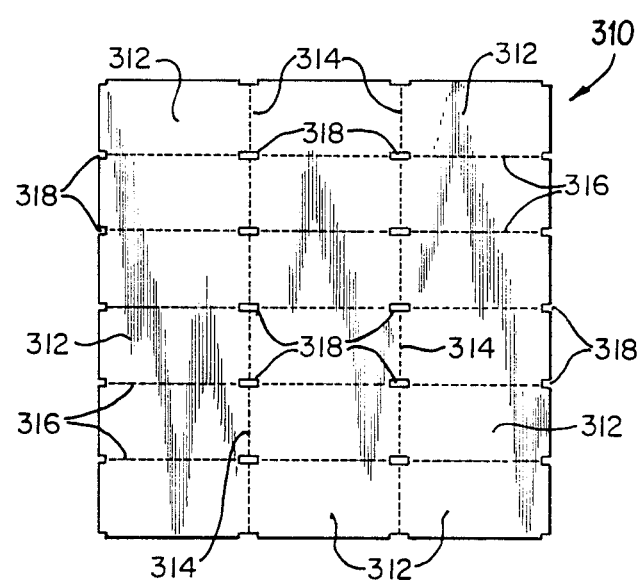
FIG. 11 is a top plan view of another arrangement of perforated packets according to the present invention.

FIG. 11 shows an alternate arrangement for the flossing packets according to the present invention. Here, packets 312 are constructed as a matrix array 310 having five rows and three columns of packets 312, much in the manner of postage stamps. Any suitably sized matrix array having m rows and n columns (m and n being integers) could be adopted for convenient manufacture. In any event, packets 312 are formed by common front and back panels which are constructed from common front and back sheets adhered to one another with appropriate glue margins similar to those described above. The sheets are then cut with vertical perforations 314, horizontal perforations 316 and cuts 318 to form packets 312. Cuts 318 also serve to sever a continuous thread of floss, which is not shown, but which would be coiled at each packet region in the manner described with respect to the earlier described embodiments.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

I claim:

1. A dental hygiene product, comprising:
   a substantially flat packet having a flat front panel and a flat back panel each formed of a flexible material and secured together along a common perimeter to define an enclosure having an interior, said packet being severable into first and second packet portions;
   a layer of tacky material disposed on a portion of an interior surface of one of said front and back panels; and
   a thread of dental floss stored within the interior of said packet, said thread having a first end secured to said first packet portion and a second end secured to said second packet portion so that, when said packet is severed into said first and second packet portions, the enclosure is ruptured whereby said thread may be withdrawn, said first and second packet portions defining first and second tabs, respectively, adapted to facilitate manual gripping of the first and second ends of the thread, said tacky material operative to initially adhere said thread in a selected configuration on the interior surface of the associated said one panel.

2. A dental hygiene product according to claim 1 wherein said first and second panels are formed of tearable material, said packet having a slit means formed at a peripheral edge for initially starting a tear that severs said packet into said first and second packet portions.

3. A dental hygiene product according to claim 1 wherein said thread is stored as a coiled configuration in said interior.

4. A dental hygiene product according to claim 1 wherein said thread is stored in a zig-zag configuration in said interior.

5. A dental hygiene product according to claim 1 where said thread is stored in a helical configuration in said interior.

6. A dental hygiene product according to claim 1 wherein said front and back panels have a common geometrical configuration and are sealed by an adhesive along at least a portion of their common perimeter, said adhesive operative to secure said first and second ends of the thread to said first and second packet portions.

7. A dental hygiene product according to claim 1 wherein said thread is ten to eighteen inches in length.

8. A dental hygiene product according to claim 1 wherein said thread is flavored.

9. A dental hygiene product, comprising:
 a plurality of substantially flat packets connected together in edge-to-edge relation to define a strip of discrete packets, said packets each being individually and successively detachable from said strip:
 each said packet having complimentary front and back panels secured together around their common perimeter to define an enclosure having an interior, each said packet being formed of a flexible and tearable material whereby each packet may be severed into first and second packet portions;
 a thread segment of dental floss stored within the interior of each said packet, each said thread segment having a first end secured to its respective said first packet portion and a second end secured to its respective said second packet portion so that, when the said packet is severed into its respective first and second packet portions, the enclosure is ruptured whereby the respective stored thread segment maybe withdrawn, said first and second packet portions thereby defining first and second tabs adapted to facilitate manual gripping of the respective ends of the thread segment: and
 slit means at a selected location between each adjacent pair of connected packets, said thread segments initially being a continuous thread, said slit means for severing adjacent thread ends of adjacent packets without severing said adjacent packets from one another to form said thread segments.

10. A dental hygiene product according to claim 9 wherein said strip has perforations between adjacent packets, said perforations operative to facilitate detachment of each successive packet from said strip.

11. A dental hygiene product according to claim 9 wherein the first and second ends of the thread segment in each packet are located at the perimeter of the respective packet, each thread end in each packet adjacent a thread end in an adjacent packet.

12. A dental hygiene product according to claim 9 wherein said strip is defined by front and back ribbons of material adhered to one another, said front ribbon defining the front panels for successive packets and said back ribbon defining the back panels for successive packets.

13. A dental hygiene product according to claim 9 wherein said packets are rectangular in shape and are connected to one another along the longer sides thereof.

14. A dental hygiene product according to claim 9 wherein said packets are rectangular in shape and are connected to one another along the shorter sides thereof.

15. A dental hygiene product according to claim 9 wherein said packets are rectangular in shape and are connected to one another to define a matrix array of packets having m rows and n columns where m and n are positive integers.

16. A dental hygiene product, comprising:
 a substantially flat packet having a flat front panel and a flat back panel each formed of a flexible material and secured together along a common perimeter to define an enclosure having an interior, said front and back panels separable from one another into first and second packet portions; and
 a thread of dental floss stored within the interior of said packet, said thread having a first end secured to said front panel and a second end secured to said back panel so that, when said packet is separated into said first and second packet portions, the enclosure is ruptured whereby said thread may be withdrawn, said first and second packet portions defining first and second tabs, respectively, adapted to facilitate manual dripping of the first and second ends of the thread.

* * * * *